(12) United States Patent
Nissl et al.

(10) Patent No.: US 7,806,918 B2
(45) Date of Patent: Oct. 5, 2010

(54) REMOVABLE STENT

(75) Inventors: Thomas Nissl, Winsen/Luhe (DE); Eric K. Mangiardi, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 10/573,950

(22) PCT Filed: Sep. 29, 2004

(86) PCT No.: PCT/US2004/031844

§ 371 (c)(1),
(2), (4) Date: Mar. 29, 2007

(87) PCT Pub. No.: WO2005/032410

PCT Pub. Date: Apr. 14, 2005

(65) Prior Publication Data

US 2007/0276463 A1 Nov. 29, 2007

(51) Int. Cl.
*A61F 2/06* (2006.01)
(52) U.S. Cl. .................... 623/1.15; 623/1.34
(58) Field of Classification Search ....... 623/1.15–1.17, 623/1.32, 1.34, 1.36, 1.23
See application file for complete search history.

(56) References Cited

U.S. PATENT DOCUMENTS

| | | | |
|---|---|---|---|
| 5,507,771 A * | 4/1996 | Gianturco | 606/198 |
| 5,741,327 A | 4/1998 | Frantzen | |
| 5,861,027 A * | 1/1999 | Trapp | 623/1.15 |
| 6,299,635 B1 * | 10/2001 | Frantzen | 623/1.17 |
| 6,330,884 B1 | 12/2001 | Kim | |
| 6,451,049 B2 | 9/2002 | Vallana et al. | |
| 6,623,518 B2 | 9/2003 | Thompson et al. | |
| 6,652,579 B1 * | 11/2003 | Cox et al. | 623/1.34 |
| 6,699,277 B1 | 3/2004 | Freidberg et al. | |
| 6,786,922 B2 * | 9/2004 | Schaeffer | 623/1.15 |
| 6,942,690 B1 * | 9/2005 | Pollock et al. | 623/1.15 |
| 7,060,093 B2 * | 6/2006 | Dang et al. | 623/1.42 |
| 2002/0022877 A1 * | 2/2002 | Mueller et al. | 623/1.16 |
| 2002/0123791 A1 * | 9/2002 | Harrison | 623/1.15 |

(Continued)

FOREIGN PATENT DOCUMENTS

EP    1157673 A2    11/2001

(Continued)

OTHER PUBLICATIONS

International Search Report for PCT/US2004/031844 completed Feb. 21, 2005.

(Continued)

*Primary Examiner*—Corrine McDermott
*Assistant Examiner*—Cheryl Miller
(74) *Attorney, Agent, or Firm*—Stoel Rives LLP

(57) ABSTRACT

The invention is relative to a stent with a tubular support frame consisting of axially successively following, interconnected annular segments which support frame is surrounded on its outside by a thread. The thread ends are guided via a deflection from the outside into support frame, where they are coupled by a connector consisting of a material visible in x-rays. Deflection is realized by two deflection elements in the form of eyelets provided on annular segments. Deflection elements are arranged on the circumference of support frame at an interval from one another and are provided on end-side annular segments, viewed in longitudinal direction of the stent.

21 Claims, 1 Drawing Sheet

U.S. PATENT DOCUMENTS

| | | | |
|---|---|---|---|
| 2002/0143386 A1 | 10/2002 | Davila et al. | |
| 2002/0198593 A1* | 12/2002 | Gomez et al. | 623/1.16 |
| 2003/0074051 A1* | 4/2003 | Freislinger Luehrs | 623/1.15 |
| 2003/0105513 A1* | 6/2003 | Moriuchi et al. | 623/1.15 |
| 2003/0176912 A1 | 9/2003 | Chuter et al. | |
| 2003/0195606 A1* | 10/2003 | Davidson et al. | 623/1.11 |
| 2004/0015228 A1* | 1/2004 | Lombardi et al. | 623/1.18 |
| 2004/0088040 A1* | 5/2004 | Mangiardi et al. | 623/1.15 |
| 2004/0176834 A1* | 9/2004 | Brown et al. | 623/1.15 |
| 2005/0004657 A1* | 1/2005 | Burgermeister | 623/1.16 |
| 2005/0107865 A1* | 5/2005 | Clifford et al. | 623/1.16 |
| 2006/0111771 A1* | 5/2006 | Ton et al. | 623/1.15 |
| 2008/0046072 A1* | 2/2008 | Laborde et al. | 623/1.34 |
| 2008/0071354 A1* | 3/2008 | Das | 623/1.15 |

FOREIGN PATENT DOCUMENTS

| | | |
|---|---|---|
| WO | WO 01/58384 | 8/2001 |

OTHER PUBLICATIONS

The Canadian Office Action for Canadian Application No. 2,540,372, mailed Feb. 22, 2008, received Mar. 3, 2008.

* cited by examiner

REMOVABLE STENT

FIELD OF INVENTION

The invention is relative to a stent with suture mediated removability features.

BACKGROUND OF THE INVENTION

Stents are used for the permanent or also only temporary splinting of body canals that are closed or constricted as a consequence of a stenosis.

Stents are introduced by catheter techniques and similar introductory aides into the intracorporal vessel in the area of the stenosis, where they function as vascular prosthesis for supporting the inner vascular walls. However, the vascular walls can be traumatized during the placing and the removal of stents. A stent can also traumatize the vessels in its placed state on account of its intrinsic movement.

The invention is therefore based on the problem of creating a stent that is improved as regards compatibility with the vessels and in the case of which the danger of injuring the vascular walls during placing or removal is reduced.

SUMMARY OF EXEMPLARY EMBODIMENTS

The invention solves this problem in a stent in accordance with the features of protective Claim 1.

According to this claim the support frame consists of at least two annular segments formed by struts that endlessly follow each other in a corrugated manner via transitional sections. Adjacent annular segments are coupled by connectors. Every second front transitional section on the end-side annular segments, viewed in the direction of the longitudinal axis of the stent, has a widened head end that projects axially opposite the adjacent transitional sections and has a convexly rounded front section and concavely rounded throat sections between the head end and the struts connected to the head end.

According to the invention the head ends are optimized by being rounded off in order to improve their atraumatic function. The rounded head ends assure a protective contact of the front ends of the stent on the vascular wall. Thus, the stent in accordance with the invention traumatizes the vascular walls less during the placing and also during the removal of a stent.

Advantageous embodiments and further developments of the stent in accordance with the invention are characterized in dependent Claims 2 to 8.

The head ends are preferably configured in a mushroom shape, in which instance the convex front sections and the concave throat sections are connected to each other by rounded edge sections.

The throat sections preferably extend over the edge-side transitional sections of the adjacent struts at least in areas in the initial state of the stent and are adapted in their contour to the contour of the transitional sections.

In another advantageous embodiment deflection elements for a thread looping around the outside of the support frame are arranged on the end-side annular segments, viewed in the direction of the longitudinal axis of the stent. The thread ends are deflected via the deflection elements into the interior of the support frame and firmly connected to each other there by a connector consisting preferably of a material visible in x-rays. In order to remove the stent the thread ends can be grasped on the connector. The thread is constricted by pulling and the looped-around annular segment of the support frame is drawn together, whereupon the stent can be removed from the body canals. This procedure substantially facilitates the explantation process of a stent. The rounded head ends provided in accordance with the invention have a positive effect, in particular during the removal of a stent. The danger of damaging the surrounding vascular walls is distinctly reduced.

The stent is extremely flexible in the non-expanded state and can readily follow the windings of body canals when being introduced into them. When widened out in the stenosis the stent is sufficiently stable to fulfill its function and to retain the necessary widened-out dimension.

As stated, the annular segments are connected to each other by connectors. In this instance the connectors are preferably designed like struts and have a longitudinal section running substantially parallel to the longitudinal axis of the stent and have a compensation section aligned transversally to the latter and configured in a U shape.

It is recommended for the practice that the U-shaped compensation section of the connectors be arranged in the area between two annular segments axially adjacent with an interval. In this embodiment the stent has a high degree of support force and is stable in its length even during external compression.

The previously mentioned features concerning the design of the connectors contribute to the fact that the stent does not experience any undesired or disadvantageous change in length in the expanded state.

The connectors extend out from the ridge area of two struts of an annular segment between two struts of the adjacent annular segment up to the transitional section of these struts. This embodiment also supports the longitudinal stability of the stent.

The individual connectors are preferably aligned in axial succession between the annular segments. In this manner a slightly elastic support frame with a high return force is produced in the expanded state (support state) of the stent.

The stent is preferably manufactured from metal. All deformable, medically possible metals and metal alloys can be used in this connection, e.g. high-grade steel, cobalt alloys (phynox), pure iron or nickel-titanium alloys.

The support frame can basically also be additionally embedded in a jacket, e.g., consisting of plastic, e.g., latex or the like.

The invention is described in detail in the following with reference made to an exemplary embodiment shown in the drawings. The invention is described in detail in the following using exemplary embodiments. Further objectives, features and advantages of the invention will be apparent from the following detailed description taken in conjunction with the accompanying drawings.

DETAILED DESCRIPTION OF AN EMBODIMENT

Figure 1:
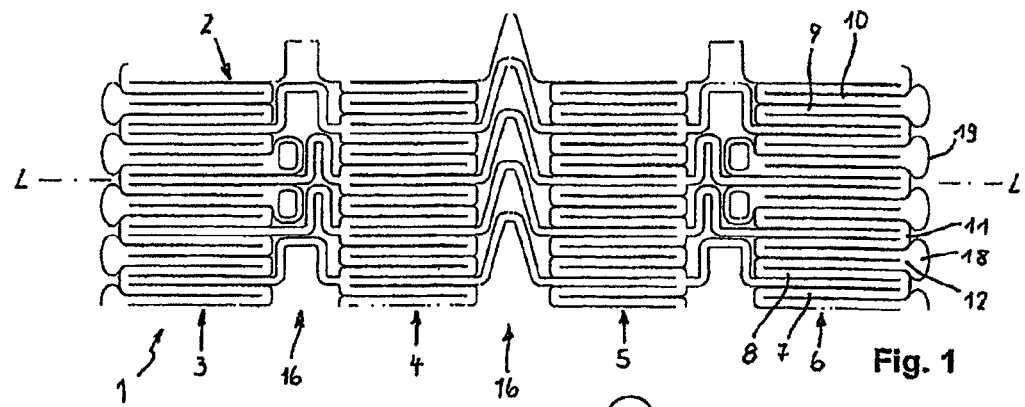
FIG. 1 shows the developed view [uncoiling] of the support frame of a stent in accordance with the invention in the non-widened out state (initial state).
Figure 2:
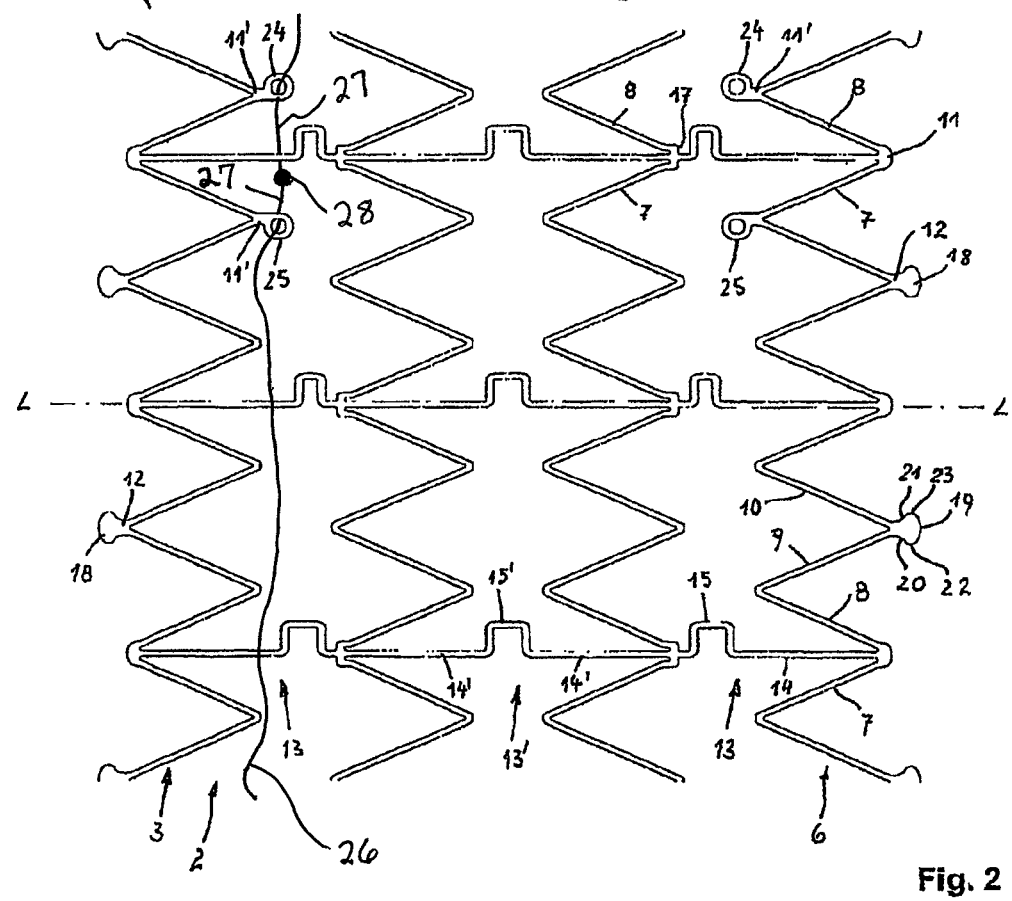
FIG. 2 shows the support frame of the stent in the widened-out state (support state).

FIGS. 1, 2 show a stent 1 in accordance with the invention in a developed view of its otherwise tubular support frame 2. Stent 1 is made of metal.

FIG. 1 shows support frame 2 in its non-widened-out initial state A whereas FIG. 2 shows support frame 2 in support state S, that is widened out relative to initial state A.

Support frame 2 consists of several, a total of four in the exemplary embodiment shown here, annular segments 3-6. These segments are formed by struts 7, 8, 9, 10 that follow each other in an endless, corrugated manner and are interconnected via transitional sections 11, 12.

Adjacent annular segments 3, 4; 4, 5 and 5, 6 are coupled by connectors 13 extending in the direction of longitudinal axis L of the stent. Connectors 13 are designed like struts and comprise a longitudinal section 14 running substantially parallel to longitudinal axis L of the stent and comprise compensation section 15 aligned transversally to the latter and configured in a U shape. It can be recognized that U-shaped or V-shaped compensation sections 15 of connectors 13 are arranged in area 16 between two annular segments 3-6 that are axially adjacent with spacing. Middle connector 13' comprises two equally long longitudinal sections 14' on both sides of its compensation section 15'.

It can also be recognized that connectors 13 are aligned in axial succession between annular segments 3-6. Connectors 13 extend in this instance from ridge area 17 of two struts 7, 8 of an annular segment 3-6 between two struts 7,8 of the adjacent annular segment to transitional section 11 of these struts 7, 8.

Every second front transitional section 12 comprises widened-out head end 18 projecting axially opposite adjacent transitional sections 11 on end-side, viewed in the direction of longitudinal axis L of the stent, annular segments 3 and 6. Each head end 18 has a convexly rounded front section 19 and concavely rounded throat sections 20, 21 between head end 18 and struts 9, 10 connected to head end 18. Head ends 18 are configured in a mushroom shape, in which instance convex front sections 19 and concave throat sections 20, 21 are connected to each other by rounded edge sections 22, 23. In this manner throat sections 20, 21 extend at least in areas over edge-side transitional sections 11 of adjacent struts 7, 8 in initial state A and cover them. The contour of throat sections 20, 21 is adapted to the contour of transitional sections 11, so that the latter are intermeshed in initial state A. Rounded head ends 18 assure a protective contact of stent 1 on the vascular wall during placing. Even when stent 1 is being removed the vascular walls are less traumatized because head ends 18 make a gentle explantation possible.

Deflection elements 24, 25 in the form of eyelets are provided on end-side annular segments 3, 6, viewed in the direction of longitudinal axis L of the stent. These eyelets are articulated in a one-piece manner on the inner side of annular segments 3, 6 in transitional area 11'. A thread 26 surrounding support frame 2 on its outside is deflected via deflection elements 23, 24 into the interior of support frame 2 where the thread ends 27 are firmly connected to each other by a connector 28 consisting of a material visible in x-rays. In order to remove stent 1 the thread ends 27 can be grasped on the connector. The thread 26 is constricted by pulling, during which the looped-around annular segment 3 or 6 is radially drawn together. Stent 1 can subsequently be removed from the body canal, during which, as stated, rounded and widened-out head ends 18 assure a gentle removal of stent 1.

LIST OF REFERENCE NUMERALS

1—stent
2—support frame
3—annular segment
4—annular segment
5—annular segment
6. annular segment
7—strut
8—strut
9—strut
10—strut
11—transitional section
11'—transitional section
12—transitional section
13—connector
13'—connector
14—longitudinal section
14'—longitudinal section
15—compensation section
15'—compensation section
16—area
17—ridge area
18—head area
19—front section
20—throat section
21—throat section
22—edge section
23—edge section
24—deflection element
25—deflection element
L—longitudinal axis of stent
A—initial state
S—support state The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A stent configured to reduce traumatization of the vessel wall, the stent comprising:
    a tubular support frame that can be expanded from an initial state to a support state, in which the tubular support frame comprises at least two annular segments that are formed by struts that are interconnected in a corrugated manner via transitional sections and in which adjacent annular segments are coupled by connectors, wherein one of the annular segments corresponds to a proximal end of the tubular support frame and one of the annular segments corresponds to a distal end of the tubular support frame, wherein every other transitional section at the proximal and distal ends of the tubular support frame has a widened head end that axially projects proximally from the proximal end and distally from the distal end and has a convexly rounded front section, concavely rounded throat sections between the head end and the struts connected to the head end, and convexly rounded edge sections extending between the convexly rounded front section and the concavely rounded throat sections, wherein the concavely rounded throat sections are configured to intermesh with, and extend at least partially over and abut, adjacent transitional sections in the initial state, each widened head end having a maximum width measured transverse to a longitudinal axis of the tubular support frame, wherein each widened head end comprises a structure that is solid across the entire maximum width, and wherein the tubular support frame further comprises a plurality of deflection elements for a thread looping around the outside of the support frame that are arranged on the annular segments at the proximal and distal ends of the support frame, wherein each deflection element comprises an eyelet configured to receive a thread therethrough.

2. A stent configured to reduce traumatization of a vessel wall, the stent comprising:
    a tubular support frame that can be expanded from an initial state to support state, in which the tubular support frame comprises at least two annular segments that are formed by struts that are interconnected in a corrugated manner via transitional sections and in which adjacent annular segments are coupled by connectors, wherein one of the annular segments corresponds to a proximal end of the tubular support frame and one of the annular segments corresponds to a distal end of the tubular support frame, wherein each strut has substantially the same length measured between respective transitional sections about the stent's circumference, wherein every other transitional section at the proximal and distal ends of the tubular support frame has a widened head end having a larger maximum width measured transverse to a longitudinal axis of the tubular support frame than a head end of an adjacent transitional section, wherein each widened head end axially projects proximally from the proximal end and distally from the distal end and has a convexly rounded front section, concavely rounded throat sections between the head end and the struts connected to the head end, and convexly rounded edge sections extending between the convexly rounded front section and the concavely rounded throat sections, wherein the concavely rounded throat sections are configured to intermesh with, and extend at least partially over and abut, adjacent transitional sections in the initial state.

3. A stent configured to reduce traumatization of a vessel wall, the stent comprising:

a tubular support frame that can be expanded from an initial state to a support state, in which the tubular support frame comprises at least two annular segments that are formed by struts that are interconnected in a corrugated manner via transitional sections and in which adjacent annular segments are coupled by connectors, wherein one of the annular segments corresponds to a proximal end of the tubular support frame and one of the annular segments corresponds to a distal end of the tubular support frame, wherein every other transitional section at the proximal and distal ends of the tubular support frame has a widened head end having a larger maximum width measured transverse to a longitudinal axis of the tubular support frame than a head end of an adjacent transitional section, wherein each widened head end axially projects proximally at the proximal end and distally at the distal end and has a convexly rounded front section, concavely rounded throat sections between the head end and the struts connected to the head end, and convexly rounded edge sections extending between the convexly rounded front section and the concavely rounded throat sections, wherein the concavely rounded throat sections are configured to intermesh with, and extend at least partially over and abut, adjacent transitional sections in the initial state, and wherein each of the struts are parallel to one another in the initial state.

4. The stent according to claim 3, further comprising a plurality of deflection elements for a thread looping around the outside of the support frame that are arranged on the annular segments at the proximal and distal ends of the support frame, wherein each deflection element comprises an eyelet configured to receive a thread therethrough.

5. The stent according to claim 4, wherein at least a portion of each deflection element is configured to be positioned adjacent to at least a portion of an adjacent connector in the initial state.

6. The stent according to claim 4, wherein each deflection element projects axially from a respective transitional section.

7. The stent according to claim 6, wherein each deflection element is configured to intermesh with, and extend at least partially over, an adjacent transitional section in the initial state.

8. The stent according to claim 4, wherein each strut comprises first and second ends, and wherein each widened head end is located at the first ends of the struts at the proximal and distal ends of the support frame and each deflection element is located at the second ends of the struts.

9. The stent according to claim 8, wherein each connector comprises a longitudinal section running substantially parallel to a longitudinal axis of the stent and a compensation section, and wherein each deflection element is configured to extend adjacent to an adjacent longitudinal section and extend between a compensation section of an adjacent annular segment and at least a portion of the second ends of adjacent struts in the initial state.

10. The stent according to claim 3, wherein each connector has a longitudinal section running substantially parallel to a longitudinal axis of the stent and comprises a compensation section aligned transversally to the latter and configured to a U or V shape.

11. The stent according to claim 10, wherein the U-shaped or V-shaped compensation sections of the connectors are arranged in an area between two axially adjacent, spaced annular segments.

12. The stent according to claim 10, wherein the longitudinal section of each connector is substantially parallel to each of the struts in the initial state.

13. The stent according to claim 3, further comprising an annular segment interconnected to an adjacent annular segment at the proximal or distal ends of the tubular support frame, wherein the connectors extend out from a ridge area of two struts of the annular segment to the transitional section of the adjacent annular segment at the proximal or distal ends of the tubular support frame.

14. The stent according to claim 3, wherein the connectors are aligned in axial succession.

15. The stent according to claim 3, wherein each strut comprises first and second ends, and wherein each head end is spaced outwardly from the first ends of adjacent struts by a distance corresponding to the concavely rounded throat sections.

16. The stent according to claim 3, wherein each widened head end axially projects further proximally at the proximal end of the tubular support frame and further distally at the distal end of the tubular support frame than an adjacent transitional section.

17. The stent according to claim 3, wherein each transitional section comprises convexly curved side edges that are configured to intermesh with adjacent concavely rounded throat sections in the initial state.

18. The stent according to claim 3, wherein the rounded edge sections of adjacent widened head ends are spaced apart from another in the initial state.

19. The stent according to claim 1, wherein a width of each widened head end measured transverse to a longitudinal axis of the tubular support frame is larger than a width of each widened head end measured along the longitudinal axis.

20. The stent according to claim 1, wherein each strut has substantially the same length measured between respective transitional sections about the stent's circumference.

21. The stent according to claim 1, wherein each widened head end comprises a solid material.

\* \* \* \* \*